(12) United States Patent
Snow et al.

(10) Patent No.: US 8,227,643 B2
(45) Date of Patent: *Jul. 24, 2012

(54) SIRTUIN 1 AND THE TREATMENT OF NEURODEGENERATIVE DISEASES

(75) Inventors: Alan D. Snow, Lynnwood, WA (US); Qubai Hu, Kirkland, WA (US); Judy A. Cam, Bellevue, WA (US)

(73) Assignee: ProteoTech, Inc., Kirkland, WA (US)

( * ) Notice: Subject to any disclaimer, the term of this patent is extended or adjusted under 35 U.S.C. 154(b) by 298 days.

This patent is subject to a terminal disclaimer.

(21) Appl. No.: 12/685,836

(22) Filed: Jan. 12, 2010

(65) Prior Publication Data

US 2011/0015272 A1    Jan. 20, 2011

Related U.S. Application Data

(63) Continuation-in-part of application No. 12/269,017, filed on Nov. 11, 2008, now abandoned, which is a continuation of application No. 10/452,851, filed on May 30, 2003, now Pat. No. 7,514,583.

(60) Provisional application No. 60/385,144, filed on May 31, 2002, provisional application No. 60/409,100, filed on Sep. 9, 2002, provisional application No. 60/412,272, filed on Sep. 20, 2002, provisional application No. 60/435,880, filed on Dec. 20, 2002, provisional application No. 60/463,104, filed on Apr. 14, 2003, provisional application No. 61/143,908, filed on Jan. 12, 2009.

(51) Int. Cl.
| | |
|---|---|
| C07C 33/00 | (2006.01) |
| C07C 49/00 | (2006.01) |
| C07C 209/00 | (2006.01) |
| C07C 211/00 | (2006.01) |
| C07C 233/00 | (2006.01) |
| C07C 239/00 | (2006.01) |
| C07C 275/00 | (2006.01) |
| A61K 31/00 | (2006.01) |

(52) U.S. Cl. ......... 568/331; 568/807; 568/809; 564/52; 564/158; 564/170; 564/175; 564/179; 564/367; 564/384; 514/598; 514/616; 514/622; 514/649; 514/650; 514/655; 514/685; 514/734

(58) Field of Classification Search .................. None
See application file for complete search history.

(56) References Cited

U.S. PATENT DOCUMENTS

| | | | | |
|---|---|---|---|---|
| 7,514,583 B2 * | 4/2009 | Snow et al. | .................... | 564/179 |
| 7,601,876 B2 * | 10/2009 | Snow et al. | .................... | 568/331 |
| 7,714,170 B2 * | 5/2010 | Snow et al. | .................... | 568/331 |

OTHER PUBLICATIONS

Arai et al., "Argyrophilic glial inclusions in the midbrain of patients with Parkinson's disease and diffuse Lewy body disease are . . . ", Neuroscience Letters 259:83-86 (1999).
Chen et al., "SIRT1 protects against microglia-dependent amyloid-beta toxicity through inhibiting NF-kappaB signaling.", J. Biol. Chem. 280(48):40364-40374 (2005).
Cho, J., and Johnson, G.V.W., "Primed phosphorylation of tau at Thr231 by glycogen synthase kinase 3β (GSK3β) plays a critical role . . . ", J. Neurochem. 88:349-358 (2004).
Chong et al., "The Sirtuin Inhibitor Nicotinamide Enhances Neuronal Cell Survival During Acute Anoxic Injury . . . ", Curr. Neurovasc. Res. 2(4):271-285 (2005).
Ewers et al., "Multicenter assessment of CSF-phosphorylated tau for the prediction of conversion of MCI", Amer. Acad. Neurology 69:2205-2212 (2007).
Fabrizio et al., "Sir2 Blocks Extreme Life-Span Extension", Cell 123:655-667 (2005).
Flood et al., "Amnestic effects in mice of four synthetic peptides homologous to amyloid β protein from patients with . . . ", Procl. Natl. Acad. Sci. 88:3363-3366 (1991).
Flood et al., "An amyloid β-protein fragment, Aβ[12-28], equipotently impairs post-training memory, processing when injected . . . ", Brain Research 663:271-276 (1994).
Fukuchi et al., "Overexpression of amyloid precursor protein alters its normal processing and is associated with neurotoxicity", (1992).
Gan, L. and Mucke, L., "Paths of convergence: sirtuins in aging and neurodegeneration", Neuron 58:10-14 (2008).
Glenner, G.G. and Wong, C.W., "Alzheimer's Disease: Initial Report of the Purification and Characterisation . . . ", Biochem. Biophys. Res. Comm. 120(3): 885-890 (1984).
Granados-Soto, V., "Pleiotropic effects of resveratrol", Drug News Perspect. 16 (5):299-307 (2003).
Green et al., "Nicotinamide Restores Cognition in Alzheimer's Disease Transgenic Mice via a Mechanism Involving Sirtuin Inhibition . . . ", J. Neurosci. 28(45):11500-11510 (2008).
Grundke-Iqbal et al., "Abnormal phosphorylation of the microtubule—associated protein τ (tau) in Alzheimer . . . ", Procl. Natl. Acad. Sci. USA 83:4913-4917 (1986).
Harrigan et al., "Beta Amyloid is Neurotoxic in Hippocampal Slice Cultures", Neurobiology of Aging 16(5):779-789 (1995).
Hsiao et al., "Correlative memory Deficits, Aβ Elevation, and Amyloid Plaques in Transgenic Mice", Science 274:99-102 (1996).
Hu et al., "Endoproteolytic Cleavage of FE65 Converts the Adaptor Protein to a Potent Suppressor of the sAPPα Pathway in Primates", J Biol Chem. 280:12548-12558 (2005).
Husby et al., "Nomenclature of Amyloid and Amyloidosis", Bull. WHO 71 (1):105-108 (1993).
Kaeberlein et al., "The SIR2/3/4 complex and SIR2 alone promote longevity in *Saccharomyces cerevisiae* by two different mechanisms", Genes & Development 13:2570-2580 (1999).
Kenyon, C., "A conserved regulatory system for aging", Cell 105:165-168 (2001).

(Continued)

*Primary Examiner* — Brian J Davis
(74) *Attorney, Agent, or Firm* — Rebecca Eagen

(57) ABSTRACT

This invention relates to bis- and tris-dihydroxyaryl compounds and their methylenedioxy analogs and pharmaceutically acceptable salts and their use in the modulation of Sirtuin 1 (Sirt1) and there use in neuroprotection for subject suffering from neurodegenerative diseases such as Alzheimer's disease, Huntington's disease, Amyotrophic lateral sclerosis, frontotemporal dementia, Parkinson's disease, including Parkinson's plus diseases such as multiple system atrophy, progressive supranuclear palsy, corticobasal degeneration and dementia with Lewy bodies, and in the manufacture of medicaments for such Sirt1 modulation and neuroprotection.

7 Claims, 3 Drawing Sheets

OTHER PUBLICATIONS

Kim et al., "SIRT1 deacetylase protects against neurodegeneration in models for Alzheimer's disease and amyotrophic lateral sclerosis", EMBO J. 26(13):3169-3179 (2007).

Kosik et al., "Microtubule-associated protein tau (τ) is a major antigenic component of paired helical filaments . . . ", Procl. Natl. Acad. Sci. USA 83:4044-4048 (1986).

Krüger et al., "Ala30Pro mutation in the gene encoding α-synuclein in Parkinson's disease", Nature Genetics 18:106-108 (1998).

Lee et al., "A-68: A Major Subunit of Paired Helical Filaments and Derivatized Forms of Normal Tau", Science 251:675-678 (1991).

Lewy, F.H., "Paralysis agitans" in Handbuch der Neurologie, M. Lawandowsky (Ed.), Berlin: Springer-Verlag pp. 920-933 (1912).

Li et al., "SirT1 Inhibition Reduces IGF-I/IRS-2/Ras/ERK1/2 Signaling and Protects Neurons", Cell metab. 8(1):38-48 (2008).

Mandybur T., "Cerebral Amyloid Angiopathy: The Vascular Pathology and Complications", Journal of Neuropathology and Experimental Neurology 45(1):79-90 (1986).

Masters et al., "Amyloid plaque core protein in Alzheimer's disease and Down syndrome", Proc. Natl. Sci. USA 82:4245-4249 (1985).

Muchowski, P.J., and Wacker, J.L., "Modulation of neurodegeneration by molecular chaperones", Nature Reviews, Neuroscience 6:11-22 (2005).

Outeiro et al., "Sirtuin 2 Inhibitors Rescue Alpha-Synuclein-Mediated Toxicity in Models of Parkinson's Disease", Science 317:516-519 (2007).

Pallos et al., "Inhibition of specific HDACs and sirtuins suppresses pathogenesis in a *Drosophila* model of Huntington's disease", Hum. Mol. Genet. 17:3767-3775 (2008).

Pardridge et al., "Amyloid Angiopathy of Alzheimer's Disease: Amino Acid Composition and Partial Sequence of a 4,200-Dalton Peptide . . . ", J. Neurochem. 49(5):1394-1401 (1987).

Pike et al., "In vitro aging of β-amyloid protein causes peptide aggregation and neurotoxicity", Brain Research 563:311-314 (1991).

Pike et al., "Structure-Activity Analyses of β-Amyloid Peptides: Contributions of the β25-35 Region to Aggregation and Neurotoxicity", J. Neurochem. 64(1):253-265 (1995).

Pillarisetti, S., "A Review of Sirt1 and Sirt1 Modulators in Cardiovascular and Metabolic Diseases", Recent Patents Cardiovasc. Drug Discov. 3:156-164 (2008).

Pollanen et al. "Pathology and Biology of the Lewy Body", Journal of Neuropathology and Experimental Neurology 52: 183-191 (1993).

Polymeropoulos et al., "Mutation in the α-Synuclein Gene Identified in families with Parkinson's Disease", Science 276:2045-2047 (1997).

Qin et al., "Neuronal SIRT1 activation as a novel mechanism underlying the prevention of Alzheimer disease amyloid neuropathology . . . ", J. Biol. Chem. 281(31):21745-21754 (2006).

Rogina, B., and Helfand, S.L., "Sir2 mediates longevity in the fly through a pathway related to calorie restriction", PNAS 101(45):15998-16003 (2004).

Sengupta et al., "Phosphorylation of Tau at Both Thr 231 and Ser 262 Is Required for Maximal Inhibition of Its Binding . . . ", Archives of Biochem. Biophys. 357(2):299-309 (1998).

Spillantini et al., "Alpha-Synuclein in filamentous inclusions of Lewy bodies from Parkinson's disease", Proc. Natl. Acad. Sci. USA 95:6469-6473 (1998).

Tanzi et al., "Protease inhibitor domain encoded by an amyloid protein precursor mRNA associated with Alzheimer's disease", Nature 331:528-532 (1988).

Tissenbaum, H.A., and Guarente, L., "Increased dosage of a sir-2 gene extends lifespan in *Caenorhabditis elegans*", Nature 410:2270230 (2001).

Ueda et al., "Molecular cloning of cDNA encoding an unrecognized component of amyloid in Alzheimer's disease", Proc. Natl. Acad. Sci. USA 90:11282-11286 (1993).

Yang et al., "A Dominant Role for FE65 (APBB1) in Nuclear Signaling", J Biol Chem. 281:4207-4214 (2006).

\* cited by examiner

A.

B.

SIRTUIN 1 AND THE TREATMENT OF NEURODEGENERATIVE DISEASES

RELATED APPLICATIONS

This application is a continuation in part of U.S. application Ser. No. 12/269,017 filed Nov. 11, 2008, now abandoned which is a continuation of U.S. application Ser. No. 10/452,851 filed on May 30, 2003, now U.S. Pat. No. 7,514,583 issued Apr. 9, 2009 which claimed priority under 35 USC 119(e) to:
(1) U.S. Provisional Application No. 60/385,144, filed May 31, 2002,
(2) U.S. Provisional Application No. 60/409,100, filed Sep. 9, 2002,
(3) U.S. Provisional Application No. 60/412,272, filed Sep. 20, 2002,
(4) U.S. Provisional Application No. 60/435,880, filed Dec. 20, 2002, and
(5) U.S. Provisional Application No. 60/463,104, filed Apr. 14, 2003. This application also claims priority under 35 USC 119(e) to U.S. Provisional Application No. 61/143,908, filed Jan. 12, 2009.

The entire contents of all of these applications are incorporated by reference into this application.

TECHNICAL FIELD

This invention relates to bis- and tris-dihydroxyaryl compounds and their methylenedioxy analogs and pharmaceutically acceptable esters, their synthesis, pharmaceutical compositions containing them, and their use in the modulation of Sirtuin 1 (Sirt1) and in the neuroprotection of a mammal suffering from a neurodegenerative disease such as Alzheimer's disease, Huntington's disease, Amyotrophic lateral sclerosis, frontotemporal dementia, Parkinson's disease, including Parkinson's plus diseases such as multiple system atrophy, progressive supranuclear palsy, corticobasal degeneration and dementia with Lewy bodies, and the use of the compounds in the manufacture of medicaments for such treatment.

BACKGROUND

Sirtuins

Sirtuins were first identified in yeast as silence information regulators (SIRs), from which the family derives its name (Rine, J and Herskowitz, I., 1987 Genetics 116:9-22). Sirtuins are class III histone deacetylases (HDACs) that consume one nicotinamide adenine dinucleotide (NAD+) for every acetyl group they remove from a protein substrate (Landry, J et al., 2000 PNAS 97(11):5807-5811). Sirtuins are phylogenetically conserved from bacteria to humans and regulate cell functions by deacetylating both histone and nonhistone targets. Sir2 in yeast (Sirt1 in mammals) is the founding member of the sirtuin gene family, and its deacetylase activity is required for chromatin silencing (Buck et al., 2004 J. Leukocyte Bio 75:939-950).

There are seven human homologs of Sirt1 (Sirt1-7). The distinct subcellular localizations of the sirtuins also contribute to their diverse functions (Gan, L and Mucke, L 2008 Neuron 58:10-14). Sirt1, Sirt6, and Sirt7 reside predominantly in the nucleus and have been implicated in genomic stability and cell proliferation. Sirt1 is the most studied among mammalian sirtuins. Sirt2, which resides mostly in the cytoplasm, is involved in mitosis and differentiation of oligodendrocytes, likely through deacetylation of tubulins. Sirt3, Sirt4, and Sirt5 are localized in mitochondria, they may play a role in energy metabolism and responses to oxidative stress.

Sirt1 and Sirt2 play important roles in aging and neurodegeneration (Gan, L and Mucke, L 2008 Neuron 58:10-14). Sir2/Sirt1 promotes replicative life-span extension in yeast (Kaeberlein, M et al., 1999 Genes and Development 13:2570-2580), C. elegans (Tissenbaum, H. A., and Guarente, L., 2001 Nature 410:227-230), and Drosophila (Rogina, B. and Helfand, S. L. 2004, PNAS 101(45):15998-16003). However, whether increased Sirt1 activity promotes longevity also in mammals fed a normal diet has not yet been reported. The most studied nongenetic strategy to extend life span is caloric restriction, which activates sirtuin pathways (Kenyon, C. 2001 Cell 105:165-168).

Abnormal accumulation of misfolded proteins appears to play a pivotal role in diverse neurodegenerative diseases. Relevant molecules include $A\beta$ peptides and tau in Alzheimer disease (AD), $\alpha$-synuclein in Parkinson's disease (PD), TDP-43 in frontotemporal dementia (FTD), and mutant huntingtin in Huntington's disease (HD) (Muchowski, P. J. and Wacker, J. L. 2005 Nature Reviews, Neuroscience 6:11-22). Recent evidence has shown that inhibition of Sir2 activity or down-regulations of Sir2/Sirt1 levels improve pathology in a Drosophila model of Huntington's disease (Pallos, J. et al., Hum Mol Genet 2008, 17:3767-3775). Inhibition of Sirt2 was shown to rescue $\alpha$-synuclein toxicity and modified inclusion morphology in a cellular model of Parkinson's disease. Genetic inhibition of Sirt2 via small interfering RNA similarly rescued $\alpha$-synuclein toxicity (Outeiro, T. F. et al., Science. 2007, 317:516-519). The role of down-regulation of sirtuin function in rescuing pathogenesis of neurodegenerative diseases has recently been linked to a mechanism that involves tau phosphorylation. Nicotinamide, a sirtuin inhibitor, restores cognition in AD transgenic mice by selective reduction of Thr231-phospho-tau (Green, K. N. et al., J Neurosci. 2008 28(45):11500-11510). This particular species of tau has been reported to interfere with microtubule polymerization (Sengupta et al., 1998 Archives of Biochem & Biophys 357(2):299-309; Cho, J. and Johnson, G. V. W. 2004 J. of Neurochem 88:349-358), and is a commonly used biomarker for AD found in CSF (Ewers et al., 2007 Neurology 69:2205-2212). Nicotinamide also dramatically increased acetylated alpha-tubulin, a primary substrate of Sirt2, and MAP2c, both of which are linked to increased microtubule stability. Resveratrol (a polyphenol found in red wines) and other structure-related compounds are Sirt1-pathway modulators (Granados-Soto, V. 2003 Drug News Perspect, 16: 299-307). Although initial research focused on the role of sirtuins in life span extension especially in lower organisms, more recent studies also show that Sir2/Sirt1 activity can impact a wide array of proteins implicated in cardiovascular and metabolic diseases (Pillarisetti, S. 2008 Recent Patents Cardiovasc Drug Discov 3:156-164) as well as neurodegenerative diseases.

The effects and regulation of sirtuins under physiological and pathological conditions appear to be extremely complex. While still under debate, an emerging hypothesis proposes that increasing Sir2/Sirt1 positively regulates replicative aging (in dividing cells), while negatively impacting chronological aging (in non-dividing cells), including neurodegenerative diseases (Fabrizio, P. et al., 2005, Cell. 123:655-67; Pallos, J. et al., Hum Mol Genet 2008, 17:3767-3775). Pharmacological agents that modulate activity and expression of sirtuins may help with defining the precise roles of sirtuins in cardiovascular and metabolic diseases as well as the production, assembly, and degradation of pathogenic proteins, elucidating the etiology of neurodegenerative diseases and opening up new avenues for therapeutic intervention.

Neurodegenerative Diseases and Neuroprotection

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al., *Proc. Natl. Acad. Sci. USA* 82:4245-4249, 1985; Husby et al., *Bull. WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., *Nature* 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913-4917, 1986; Kosik et al., *Proc. Natl. Acad. Sci. USA* 83:4044-4048, 1986; Lee et al., *Science* 251:675-678, 1991). The pathological hallmark of Alzheimer's disease is therefore the presence of "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987)

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., *Br. Res.* 563:311-314, 1991; *J. Neurochem.* 64:253-265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al., *Neurobiol. Aging* 16:779-789, 1995) and induces nerve cell death in transgenic mice (Games et al., *Nature* 373:523-527, 1995; Hsiao et al., *Science* 274:99-102, 1996). Injection of the Alzheimer's Aβ into rat brain also causes memory impairment and neuronal dysfunction (Flood et al., *Proc. Natl. Acad. Sci. USA* 88:3363-3366, 1991; *Br. Res.* 663:271-276, 1994).

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of α-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in α-synuclein causing familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998).

In AD, inflammatory reactions in the supporting neuronal cell network, especially microglia and astrocytes, can contribute to neuronal cell death. Overexpression of Sirt1 was found to inhibit NF-κB and block the neurotoxicity of beta-amyloid accumulation, resulting in neuroprotection (Chen, J., et al 2005 *J. Biol. Chem.* 280(48):40364-40374). In another study, AD transgenic mice, subjected to caloric restriction were found to have elevated Sirt1 activity in brain tissue and the corresponding classical Aβ neuropathology was prevented. This same study also demonstrated that in CHO-APPswe cells, that Sirt1 expression promoted α-secretase activity and attenuated Aβ peptide generation (Qin, W., et al., 2006 *J. Biol. Chem.* 281(31):21745-21754). A more recent paper describes a study where mouse models for AD and amyotrophic lateral sclerosis (ALS) treated with Sirt1 activating molecules promoted neuronal survival (Kim, D., et al. 2007 *EMBO J* 26:3169-3179).

In contrast to these studies, Chong Z., et al 2005 *Curr Neurovasc Res.* 2(4):271-285 showed that the sirtuin inhibitor nicotinamide enhanced neuronal cell survival. Li, Y., et al., 2008 *Cell Metab.* 8(1):4-5 have also shown that Sirt1 inhibition is neuroprotective.

In a Parkinson's disease model system, Outeiro, T. F., et al., (2007 *Science* 317:516-519) reported that human neuroglioma cell cultures induced for α-synuclein mediated toxicity could be rescued by treatment with siRNA inhibitors of Sirt2. In a *Drosophila* Huntington's disease model, flies heterozygous for Sir2 (ortholog of Sirt1) null mutations exhibited improved survival (Pallos, J., et al 2008 *Hum. Mol. Gen.* 17(3):3767-3775).

The common thread which links these diseases is that either an accumulated misfolded protein or something else in the brain exhibits neurotoxic properties which contributes to the progression of the disease and manifestation of symptoms. Studies have shown that modulation of sirtuin1 exhibits neuroprotective effects in many different models of these neurodegenerative diseases. Therefore, compounds which modulate levels of sirtuin1 could be therapeutically beneficial in the management of neurodegenerative diseases such as Alzheimer's disease, Huntington's disease, Amyotrophic lateral sclerosis (ALS), frontotemporal dementia (FTD), Parkinson's disease, including Parkinson's plus diseases such as multiple system atrophy (MSA), progressive supranuclear palsy (PSP), corticobasal degeneration (CBD) and dementia with Lewy bodies (DLB).

SUMMARY OF THE INVENTION

In a first aspect, this invention is a method for modulating sirtuin1 comprising contacting human sirtuin 1 with a compound of this invention.

In one embodiment, the compounds of this invention are compounds of the formula:

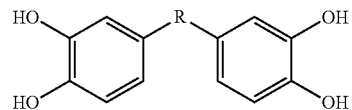

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group.

In another embodiment, the compounds of this invention are: 3,4,3',4'-tetrahydroxybenzoin (compound 1); 3,4,3',4'-tetrahydroxydesoxybenzoin (compound 2); 3,4,3',4'-tetrahydroxydiphenylmethane (compound 3); 1,2-bis(3,4-dihydroxyphenyl)ethane (compound 4); 1,3-bis(3,4-dihydroxyphenyl)propane (compound 5); 3,4,3',4'-tetrahydroxychalcone (compound 6); 3,5-bis(3,4-dihydroxyphenyl)-1-methyl-2-pyrazoline (compound 7); 4,6-bis(3,4-dihydroxyphenyl)-3-cyano-2-methylpyridine (compound 8); 1,4-bis(3,4-dihydroxybenzyl)piperazine (compound 9); N,N'-bis(3,4-dihydroxybenzyl)-N,N'-dimethylethylenediamine (compound 10); 2,5-bis(3,4-dihydroxybenzyl)-2,5-diaza[2.2.1]bicycloheptane (compound 11); N,N'-bis(3,4-dihydroxybenzyl)-trans-1,2-diaminocyclohexane (compound 12); N,N'-bis(3,4-dihydroxybenzyl)-trans-1,4-diaminocyclohexane (compound 13); N,N'-bis(3,4-dihydroxybenzyl)-cis-1,3-bis(aminomethyl)cyclohexane (compound 14); N-(3,4-dihydroxybenzyl)proline 3,4-dihydroxybenzylamide (compound 15); 2-(3,4-dihydroxybenzyl)isoquinoline-3-carboxylic acid 3,4-dihydroxyphenethylamide (compound 16); 2,6-bis(3,4-dihydroxybenzyl)cyclohexanone (compound 17); 3,5-bis(3,4-dihydroxybenzyl)-1-methyl-4-piperidinone (compound 18); 2,4-bis(3,4-dihydroxybenzyl)-3-tropinone (compound 19); tris(3,4-dihydroxybenzyl)methane (compound 20); α-(3,4-dihydroxybenzamido)-3,4-dihydroxycinnamic acid 3,4-dihydroxybenzyl amide (compound 21); 4-(3,4-dihydroxybenzylaminomethylene)-2-(3,4-dihydroxyphenyl)oxazolin-5-one (compound 22); 1,4-bis(3,4-dihydroxybenzoyl)piperazine (compound 23); N,N'-bis(3,4-dihydroxybenzoyl)-N,N'-dimethylethylenediamine (compound 24); 2,5-bis(3,4-dihydroxybenzoyl)-2,5-diaza[2.2.1]bicycloheptane (compound 25); N,N'-bis(3,4-dihydroxybenzoyl)-trans-1,2-diaminocyclohexane (compound 26); N,N'-bis(3,4-dihydroxybenzoyl)-cis-1,3-bis(aminomethyl)cyclohexane (compound 27); 3,6-bis(3,4-dihydroxybenzyl)-2,5-diketopiperazine (compound 28); 3,6-bis(3,4-dihydroxybenzylidene)-1,4-dimethyl-2,5-diketopiperazine (compound 29); N-(3,4-dihydroxyphenylacetyl)proline 3,4-dihydroxyanilide (compound 30); 2,3-bis(3,4-dihydroxyphenyl)butane (compound 31); 1,3-bis(3,4-dihydroxybenzyl)benzene (compound 32); 1,4-bis(3,4-dihydroxybenzyl)benzene (compound 33); 2,6-bis(3,4-dihydroxybenzyl)pyridine (compound 34); 2,5-bis(3,4-dihydroxybenzyl)thiophene (compound 35); 2,3-bis(3,4-dihydroxybenzyl)thiophene (compound 36); 1,2-bis(3,4-dihydroxyphenyl)cyclohexane (compound 37); 1,4-bis(3,4-dihydroxyphenyl)cyclohexane (compound 38); 3,7-bis(3,4-dihydroxyphenyl)bicyclo[3.3.0]octane (compound 39); 2,3-bis(3,4-dihydroxyphenyl)-1,7,7-trimethylbicyclo[2.2.1]heptane (compound 40); 1,2-bis(3,4-dihydroxyphenoxy)ethane (compound 41); 1,3-bis(3,4-dihydroxyphenoxy)propane (compound 42); trans-1,2-bis(3,4-dihydroxyphenoxy)-cyclopentane (compound 43); N-(3,4-dihydroxybenzyl)-3-(3,4-dihydroxyphenoxy)-2-hydroxypropylamine (compound 44); 3,4-dihydroxyphenoxyacetic acid 3,4-dihydroxyanilide (compound 45); 3,4-dihydroxyphenoxyacetic acid 3,4-dihydroxybenzylamide (compound 46); 3,4-dihydroxyphenoxyacetic acid 3,4-dihydroxyphenethylamide (compound 47); 3,4-dihydroxybenzoic acid p-(3,4-dihydroxyphenoxy)anilide (compound 48); 3,4-dihydroxybenzoic acid o-(3,4-dihydroxyphenoxy)anilide (compound 49); 2,6-bis(3,4-dihydroxyphenoxy)pyridine (compound 50), 3,4-dihydroxybenzoic acid 3,4-dihydroxyanilide (compound 51); 3,4-dihydroxybenzoic acid 3,4-dihydroxybenzylamide (compound 52); 3,4-dihydroxybenzoic acid 3,4-dihydroxyphenethylamide (compound 53); 3,4-dihydroxyphenylacetic acid 3,4-dihydroxyanilide (compound 54); 3,4-dihydroxyphenylacetic acid 3,4-dihydroxybenzylamide (compound 55); 3,4-dihydroxyphenylacetic acid 3,4-dihydroxyphenethylamide (compound 56); 3-(3,4-dihydroxyphenyl)propionic acid 3,4-dihydroxyanilide (compound 57); 3-(3,4-dihydroxyphenyl)propionic acid 3,4-dihydroxybenzylamide (compound 58); 3-(3,4-dihydroxyphenyl)propionic acid 3,4-dihydroxyphenethylamide (compound 59); 3,4-dihydroxycinnamic acid 3,4-dihydroxyanilide (compound 60); 3,4-dihydroxycinnamic acid 3,4-dihydroxybenzylamide (compound 61); 3,4-dihydroxycinnamic acid 3,4-dihydroxyphenethylamide (compound 62); oxalic acid bis(3,4-dihydroxyanilide) (compound 63); oxalic acid bis(3,4-dihydroxybenzylamide) (compound 64); oxalic acid bis(3,4-dihydroxyphenethylamide) (compound 65); succinic acid bis (3,4-dihydroxyanilide) (compound 66); succinic acid bis(3,4-dihydroxybenzylamide) (compound 67); succinic acid bis (3,4-dihydroxyphenethylamide) (compound 68); maleic acid bis(3,4-dihydroxyanilide) (compound 69); maleic acid bis(3,4-dihydroxybenzylamide) (compound 70); fumaric acid bis (3,4-dihydroxyanilide) (compound 71); fumaric acid bis(3,4-dihydroxybenzylamide) (compound 72); bis(3,4-dihydroxybenzyl)amine (compound 73); N-(3,4-dihydroxybenzyl)-3,4-dihydroxyphenethylamine (compound 74); tris(3,4-dihydroxybenzyl)amine (compound 75); 1,3-bis(3,4-dihydroxyphenyl)urea (compound 76); 1-(3,4-dihydroxyphenyl)-3-(3,4-dihydroxybenzyl)urea (compound 77); 1-(3,4-dihydroxyphenyl)-3-(3,4-dihydroxyphenethyl)urea (compound 78); 3-deoxy-3-(3,4-dihydroxybenzyl)aminoepicatechin (compound 79); 3-deoxy-3-(3,4-dihydroxyphenethyl)aminoepicatechin (compound 80); 2,3,6,7-tetrahydroxy-9,10-epoxy-9,10-dihydroacridine (compound 81); 10-aminoanthracene-1,2,7,8-tetraol (compound 82); acridine-1,2,6,7-tetraol (compound 83); phenoxazine-2,3,7,8,10-pentaol (compound 84); dibenzo[c,f][2,7]napthyridine-2,3,10,11-tetraol (compound 85); and 6-methyl-5,6,6a,7-tetrahydro-4H-dibenzo[de,g]quinoline-2,10,11-triol (compound 86); the methylenedioxy analogs and pharmaceutically acceptable esters of compounds and the pharmaceutically acceptable salts of the compounds.

In another aspect, this invention is a method of neuroprotection for a mammal suffering from a neurodegenerative disease the method comprising administration of a compound of this invention to the mammal suffering from a neurodegenerative disease where the neurodegenerative disease is selected from the group consisting of Alzheimer's disease, Huntington's disease, Amyotrophic lateral sclerosis (ALS), frontotemporal dementia (FTD), Parkinson's disease, including Parkinson's plus diseases such as multiple system atrophy (MSA), progressive supranuclear palsy (PSP), corticobasal degeneration (CBD) and dementia with Lewy bodies (DLB).

In another aspect, this invention is the use of a compound of the invention in the manufacture of a medicament for the providing neuroprotection for a mammal suffering from neurodegenerative diseases where the neurodegenerative disease is selected from the group consisting of Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) and dementia with Lewy bodies (DLB).

In another aspect, this invention is the use of a compound of the invention in the manufacture of a medicament for modulating sirtuin1 comprising contacting human sirtuin 1 with a compound of this invention.

DETAILED DESCRIPTION OF THE INVENTION

Figure 1:
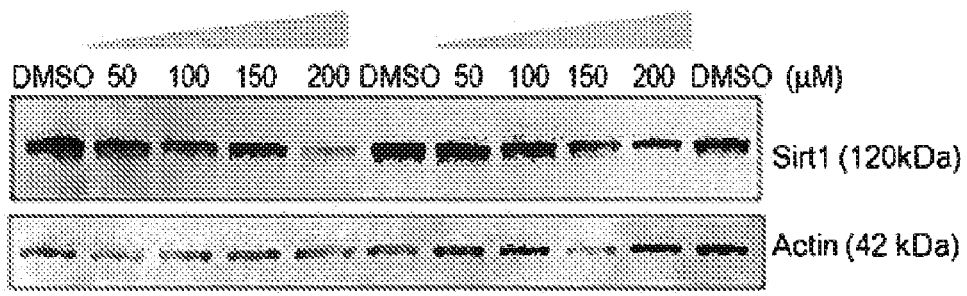
FIG. 1 is a photo and a graph showing effects of compound DC-0051 on expression of Sirt1 in cultured human embryonic kidney 293 cells that stably transfected with the human wild type APP isoform 695 (HEK293 APP cells) as assessed by Western analysis.
Figure 1:
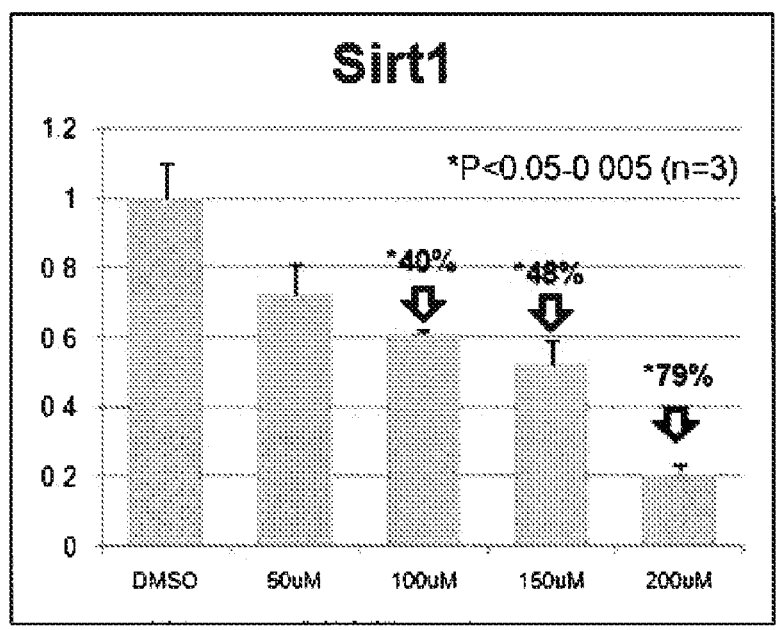

The bis- and tris-dihydroxyaryl compounds and their methylenedioxy analogs and pharmaceutically acceptable esters, and pharmaceutically acceptable salts thereof are illustrated in the parent application. The parent application also discloses the synthesis of the compounds and the formulation of pharmaceutical compositions. The entire contents of all of these applications are incorporated by reference into this application.

DEFINITIONS

The term "modulation" is art-recognized and refers to up regulation (i.e., activation or stimulation), down regulation (i.e., inhibition or suppression) of a response, or the two in combination or apart.

"Sirtuin modulation" refers to either changing the activity of a sirtuin protein or changing the amount of the sirtuin protein present.

A "modulating compound" includes both compounds that function as sirtuins activators and can also include compounds that inhibit the activity of the sirtuin protein or reduce the amount of protein present.

"Activating a sirtuin protein" refers to the action of producing an activated sirtuin protein, i.e., a sirtuin protein that is capable of performing at least one of its biological activities with an increase of activity or an increase in the amount of the protein. Biological activities of sirtuin proteins include deacetylation, e.g., of histones and p53; extending lifespan; increasing genomic stability; and silencing transcription.

"Sirtuin inhibition" refers to either decreasing the activity of a sirtuin protein or reducing the amount of protein present.

The term "prophylactic" or "therapeutic" treatment is art recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

"Neuroprotection" or "neuroprotective" refers to the ability of a compound to protect, reduce, alleviate, ameliorate, and/or attenuate damage to nerve cells (neurodegeneration).

The compounds of the invention, are referred to generally as bis- and tris-dihydroxyaryl compounds, or sometimes just as "dihydroxyaryl compounds". It will be noted that compound #84 has an additional hydroxy group, but does have two dihydroxyaryl groups; while compound #86 has only one dihydroxyaryl group but has an additional phenolic hydroxyl moiety. Compounds are illustrated in the parent application and referred to herein either as compound 1 or using the nomenclature DC-0001.

"Pharmaceutically acceptable esters" refers to the compounds of this invention where the hydroxyl moieties of the dihydroxyaryl groups of the compounds are esterified with an acid or acids that result in a pharmaceutically acceptable poly(ester). The compounds are referred to as DC-0001C to DC-0086C; but it should be understood that the depiction of acetyl esters is merely illustrative, and all pharmaceutically acceptable esters are included within this invention. The ester groups are expected to serve as intermediate protecting groups for the hydroxyl moieties and therefore the pharmaceutically acceptable esters are expected to serve as effective prodrugs for their underlying bis- and tris-dihydroxyaryl compounds.

Chemical structures for each of the compounds of this invention (with the note that the acetates are shown as representative of the pharmaceutically acceptable esters as a class) are shown in the parent application. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3,4-dihydroxyphenyl)-3,4-dihydroxybenzamide"). However, the names used are believed to be readily understood by a person of ordinary skill in the art.

"Pharmaceutically acceptable salt" means a salt that is pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A "therapeutically effective amount" in general means the amount that, when administered to a subject or animal for treating a disease, is sufficient to affect the desired degree of treatment for the disease. A "therapeutically effective amount" or a "therapeutically effective dosage" preferably provides neuroprotection to a subject suffering from a neurodegenerative disease relative to an untreated subject. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

In a first aspect, this invention is a method for modulating sirtuin1 comprising contacting human sirtuin 1 with a compound of this invention.

In one embodiment, the compounds of this invention are compounds of the formula:

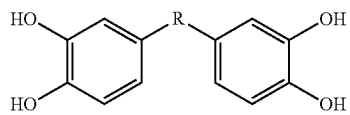

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group.

In another embodiment, the compounds of this invention are: 3,4,3',4'-tetrahydroxybenzoin (compound 1); 3,4,3',4'-tetrahydroxydesoxybenzoin (compound 2); 3,4,3',4'-tetrahydroxydiphenylmethane (compound 3); 1,2-bis(3,4-dihydroxyphenyl)ethane (compound 4); 1,3-bis(3,4-dihydroxyphenyl)propane (compound 5); 3,4,3',4'-tetrahydroxychalcone (compound 6); 3,5-bis(3,4-dihydroxyphenyl)-1-methyl-2-pyrazoline (compound 7); 4,6-bis(3,4-dihydroxyphenyl)-3-cyano-2-methylpyridine (compound 8); 1,4-bis(3,4-dihydroxybenzyl)piperazine (compound 9); N,N'-bis(3,4-dihydroxybenzyl)-N,N'-dimethylethylenediamine (compound 10); 2,5-bis(3,4-dihydroxybenzyl)-2,5-diaza[2.2.1]bicycloheptane (compound 11); N,N'-bis(3,4-dihydroxybenzyl)-trans-1,2-diaminocyclohexane (compound 12); N,N'-bis(3,4-dihydroxybenzyl)-trans-1,4-diaminocyclohexane (compound 13); N,N'-bis(3,4-dihydroxybenzyl)-cis-1,3-bis(aminomethyl)cyclohexane (compound 14); N-(3,4-dihydroxybenzyl)proline 3,4-dihydroxybenzylamide (compound 15); 2-(3,4-dihydroxybenzyl)isoquinoline-3-carboxylic acid 3,4-dihydroxyphenethylamide (compound 16); 2,6-bis(3,4-dihydroxybenzyl)cyclohexanone (compound 17); 3,5-bis(3,4-dihydroxybenzyl)-1-methyl-4-piperidinone (compound 18); 2,4-bis(3,4-dihydroxybenzyl)-3-tropinone (compound 19); tris(3,4-dihydroxybenzyl)methane (compound 20); α-(3,4-dihydroxybenzamido)-3,4-dihydroxycinnamic acid 3,4-dihydroxybenzyl amide (compound 21); 4-(3,4-dihydroxybenzylaminomethylene)-2-(3,4-dihydroxyphenyl)oxazolin-5-one (compound 22); 1,4-bis(3,4-dihydroxybenzoyl)piperazine (compound 23); N,N'-bis(3,4-dihydroxybenzoyl)-N,N'-dimethylethylenediamine (compound 24); 2,5-bis(3,4-dihydroxybenzoyl)-2,5-diaza[2.2.1]bicycloheptane (compound 25); N,N'-bis(3,4-dihydroxybenzoyl)-trans-1,2-diaminocyclohexane (compound 26); N,N'-bis(3,4-dihydroxybenzoyl)-cis-1,3-bis(aminomethyl)cyclohexane (compound 27); 3,6-bis(3,4-dihydroxybenzyl)-2,5-diketopiperazine (compound 28); 3,6-bis(3,4-dihydroxybenzylidene)-1,4-dimethyl-2,5-diketopiperazine (compound 29); N-(3,4-dihydroxyphenylacetyl)proline 3,4-dihydroxyanilide (compound 30); 2,3-bis(3,4-dihydroxyphenyl)butane (compound 31); 1,3-bis(3,4-dihydroxybenzyl)benzene (compound 32); 1,4-bis(3,4-dihydroxybenzyl)benzene (compound 33); 2,6-bis(3,4-dihydroxybenzyl)pyridine (compound 34); 2,5-bis(3,4-dihydroxybenzyl)thiophene (compound 35); 2,3-bis(3,4-dihydroxybenzyl)thiophene (compound 36); 1,2-bis(3,4-dihydroxyphenyl)cyclohexane (compound 37); 1,4-bis(3,4-dihydroxyphenyl)cyclohexane (compound 38); 3,7-bis(3,4-dihydroxyphenyl)bicyclo[3.3.0]octane (compound 39); 2,3-bis(3,4-dihydroxyphenyl)-1,7,7-trimethylbicyclo[2.2.1]heptane (compound 40); 1,2-bis(3,4-dihydroxyphenoxy)ethane (compound 41); 1,3-bis(3,4-dihydroxyphenoxy)propane (compound 42); trans-1,2-bis(3,4-dihydroxyphenoxy)-cyclopentane (compound 43); N-(3,4-dihydroxybenzyl)-3-(3,4-dihydroxyphenoxy)-2-hydroxypropylamine (compound 44); 3,4-dihydroxyphenoxyacetic acid 3,4-dihydroxyanilide (compound 45); 3,4-dihydroxyphenoxyacetic acid 3,4-dihydroxybenzylamide (compound 46); 3,4-dihydroxyphenoxyacetic acid 3,4-dihydroxyphenethylamide (compound 47); 3,4-dihydroxybenzoic acid p-(3,4-dihydroxyphenoxy)anilide (compound 48); 3,4-dihydroxybenzoic acid o-(3,4-dihydroxyphenoxy)anilide (compound 49); 2,6-bis(3,4-dihydroxyphenoxy)pyridine (compound 50), 3,4-dihydroxybenzoic acid 3,4-dihydroxyanilide (compound 51); 3,4-dihydroxybenzoic acid 3,4-dihydroxybenzylamide (compound 52); 3,4-dihydroxybenzoic acid 3,4-dihydroxyphenethylamide (compound 53); 3,4-dihydroxyphenylacetic acid 3,4-dihydroxyanilide (compound 54); 3,4-dihydroxyphenylacetic acid 3,4-dihydroxybenzylamide (compound 55); 3,4-dihydroxyphenylacetic acid 3,4-dihydroxyphenethylamide (compound 56); 3-(3,4-dihydroxyphenyl)propionic acid 3,4-dihydroxyanilide (compound 57); 3-(3,4-dihydroxyphenyl)propionic acid 3,4-dihydroxybenzylamide (compound 58); 3-(3,4-dihydroxyphenyl)propionic acid 3,4-dihydroxyphenethylamide (compound 59); 3,4-dihydroxycinnamic acid 3,4-dihydroxyanilide (compound (30); 3,4-dihydroxycinnamic acid 3,4-dihydroxybenzylamide (compound 61); 3,4-dihydroxycinnamic acid 3,4-dihydroxyphenethylamide (compound 62); oxalic acid bis(3,4-dihydroxyanilide) (compound 63); oxalic acid bis(3,4-dihydroxybenzylamide) (compound 64); oxalic acid bis(3,4-dihydroxyphenethylamide) (compound 65); succinic acid bis(3,4-dihydroxyanilide) (compound 66); succinic acid bis(3,4-dihydroxybenzylamide) (compound 67); succinic acid bis(3,4-dihydroxyphenethylamide) (compound 68); maleic acid bis(3,4-dihydroxyanilide) (compound 69); maleic acid bis(3,4-dihydroxybenzylamide) (compound 70); fumaric acid bis(3,4-dihydroxyanilide) (compound 71); fumaric acid bis(3,4-dihydroxybenzylamide) (compound 72); bis(3,4-dihydroxybenzyl)amine (compound 73); N-(3,4-dihydroxybenzyl) 3,4-dihydroxyphenethylamine (compound 74); tris(3,4-dihydroxybenzyl)amine (compound 75); 1,3-bis(3,4-dihydroxyphenyl)urea (compound 76); 1-(3,4-dihydroxyphenyl)-3-(3,4-dihydroxybenzyl)urea (compound 77); 1-(3,4-dihydroxyphenyl)-3-(3,4-dihydroxyphenethyl)urea (compound 78); 3-deoxy-3-(3,4-dihydroxybenzyl)aminoepicatechin (compound 79); 3-deoxy-3-(3,4-dihydroxyphenethyl)aminoepicatechin (compound 80); 2,3,6,7-tetrahydroxy-9,10-epoxy-9,10-dihydroacridine (compound 81); 10-aminoanthracene-1,2,7,8-tetraol (compound 82); acridine-1,2,6,7-tetraol (compound 83); phenoxazine-2,3,7,8,10-pentaol (compound 84); dibenzo[c,f][2,7]napthyridine-2,3,10,11-tetraol (compound 85); and 6-methyl-5,6,6a,7-tetrahydro-4H-dibenzo[de,g]quinoline-2,10,11-triol (compound 86); the methylenedioxy analogs and pharmaceutically acceptable esters of compounds and the pharmaceutically acceptable salts of the compounds.

In another aspect, this invention is a method of neuroprotection for a mammal suffering from a neurodegenerative disease the method comprising administration of a compound of this invention to the mammal suffering from a neurodegenerative disease where the neurodegenerative disease is selected from the group consisting of Alzheimer's disease, Huntington's disease, Amyotrophic lateral sclerosis (ALS), frontotemporal dementia (FTD), Parkinson's disease, including Parkinson's plus diseases such as multiple system atrophy (MSA), progressive supranuclear palsy (PSP), corticobasal degeneration (CBD) and dementia with Lewy bodies (DLB).

In another aspect, this invention is the use of a compound of the invention in the manufacture of a medicament for the providing neuroprotection for a mammal suffering from neurodegenerative diseases where the neurodegenerative disease is selected from the group consisting of Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) and dementia with Lewy bodies (DLB).

In another aspect, this invention is the use of a compound of the invention in the manufacture of a medicament for modulating sirtuin1 comprising contacting human sirtuin 1 with a compound of this invention.

The following non-limiting Examples are given by way of illustration only and are not considered a limitation of this invention, many apparent variations of which are possible without departing from the spirit or scope thereof.

Example 1

Dose-Dependent Reduction of Sirt1 in Cell Cultures Treated with Compounds DC-0051 and DC-0051C as Assessed by Western Analysis 1) cDNA Constructs, Cell Cultures and Stable Transfected Cell Lines Mammalian expression constructs, pCA-APP695 and pcDNA3.1-APP695-myc, were obtained from previous studies described by Fukuchi et al. (1992) and Yang et al. (2006), respectively. pCA-APP695 contains the cDNA sequence encoding for the human full-length APP695, and is driven by a chicken actin promoter. pcDNA3.1-APP695-myc was generated by subcloning of an APP695 cDNA fragment from pCA-APP695 into the BamHI and EcoRI sites of the pcDNA3.1-myc/His vector (Invitrogen), which is driven by a cytomegalovirus immediate-early promoter.

Two cell lines stably transfected with pCA-APP695 and pcDNA3.1-APP695-myc were generated to assess APP processing in cell cultures. Human Embryonic Kidney (HEK) 293 cells (ATCC #CRL-1573), and human brain neuroblastoma cells, SK—N—SH (ATCC #HTB-11), were employed to generate the APP stable cell lines. Cells were routinely cultured in a regular growth media (RGM) that contained Dulbecco's Modified Eagle Medium (DMEM) (Invitrogen) supplemented with 10% fetal bovine serum at 37° C. in a cell culture incubator supplemented with 5% CO2. HEK293 and SK—N—SH cells were grown to 70-80% confluence in 35 mm dishes, and transfected with pCA-APP695, and pcDNA3.1-APP695-myc, respectively. Transfection was mediated by polyethylenimines (Polysciences, Inc.) as described by Hu et al. (2005). Twenty-four hours after transfection, cells were plated at low density (400-2000 cells/plate), and grown in RGM containing 0.6-0.8 mg/ml G418 (Invitrogen) to select stable colonies. After two weeks, stable colonies were picked, and sub-cultured. Stable expression of APP was confirmed by Western analysis of conditioned media for secreted APP with a monoclonal antibody 6E10 (Covance), and of cell lysates for intracellular APP with an anti-APP C-terminal polyclonal antibody (Sigma). The stable canines were maintained by periodical selection with G418-containing RGM. HEK293 cells stably transfected with pCA-APP695 are referred as HEK293-APP cells, while SK—N—SH cells stably transfected with pcDNA3.1-APP695-myc are referred as SKNSH-APP cells.

2) Treatment of Cultured Cells with DC-0051 and DC-0051-C

Five hundred-micromolar stock solutions of compounds DC-0051 and DC-0051-C were prepared in DMSO, aliquoted and stored at −80° C. before use. On the day before treatment, HEK293-APP and SKNSH-APP cells were plated in 6-well culture plates with low IgG growth media [MEM+10% of low IgG fetal bovine serum (Invitrogen)]. The plating density should allow cells to reach 80-95% of confluence on next day. Upon treatment, cell culture media were replaced with 1.6 ml per well of low IgG growth media containing freshly-diluted peptides. Cells were incubated at 37° C. in a cell culture incubator for 19-20 hours. After incubation, conditioned media was collected, and centrifuged at 8000×g for 10 min at 4° C. to remove cell debris. Cell lysates were collected for Western analysis. Briefly, cell monolayer was washed once with PBS, and directly lysed in 200 µl of 2× Laemmli sample buffer (75 mM Tris-HCl, pH 8.4, 4% SDS, 20% glycerol, 50 mM DTT, 0.004% bromphenol blue) on ice for 15 min. Lysates were collected into a tube, boiled at 100° C. for 10 min without centrifugation, and stored at −80° C. for Western analysis.

3) Western Blotting

Cellular proteins in lysates were separated in 4-12% Bis/Tris Criterion XT gels (Bio-Rad), with buffer systems recommended by the manufacturer. After electrophoresis, proteins bands were transferred onto Immobilon-PSQ membranes using Bio-Rad Criterion™ Blotters, and a transfer buffer system (Bio-Rad). Transfer was conducted at 0.4 A (constant) for 90-120 min. All transferred membranes were blocked with 5% milk in PBS+0.05% Tween-20 for 30-60 min at room temperature, and incubated with an anti-human Sirt1 mouse monoclonal antibody (clone 3H10.2; 1:1000; Upstate/Millipore) for overnight at 4° C., and with HRP-conjugated secondary antibody (Vector) at 1:4000 at room temperature for 2 h. The membranes were then stripped with a Restore Western Blot Stripping Buffer (Thermo Scientific) for 20-30 min at room temperature, blocked and re-probed for β-actin with monoclonal antibody C4 (1:200,000; Sigma), or for p35 with a rabbit polyclonal antibody (1:2000; Santa Cruz Biotechnology). Protein bands were visualized with an ECL system (GE Healthcare) by exposing to autoradiography films (GE Healthcare). PhotoShop was used for image scanning and processing. Quantitation of relative intensities of protein bands on autoradiographic films was performed by image quantification with the ScionImage software downloaded from http://www.scioncorp.com.

4) Compounds DC-0051 and DC-0051C Reduce Levels of Endogenous Sirt1 in HEK293-APP and SKNSH-APP Cell Cultures FIGS. 1A-B show that compound DC-0051 reduce levels of endogenous Sirt1 in HEK293-APP cell cultures as assessed by Western analysis. (A) HEK293-APP cells were treated with 0 (DMSO vehicle control), 50, 100, 150, and 200 µM of DC-0051 in 6-well plates for 19 hrs. Each condition was in triplicate (only duplicate was shown). After incubation, cell lysates were collected and analyzed by Western analysis for Sirt1 crop panel). The membrane was then stripped and re-probed for beta-actin (Bottom panel). Reduced levels of Sirt1 were found in cells treated with compound DC-0051, when compared to DMSO vehicle control. The reduction was dose-dependent. In contrast, levels of beta-actin were not changed. (B) Quantitative densitometry analysis of (A) was performed. The results showed that a 40-79% significant reduction of Sirt1 levels was observed in lysates of cells treated with 100-200 μM of DC-0051 (P<0.05-0.005), when compared to controls. The results suggest that compound DC-0051 can reduce levels of Sirt1 in the cell line tested.

Figure 2:
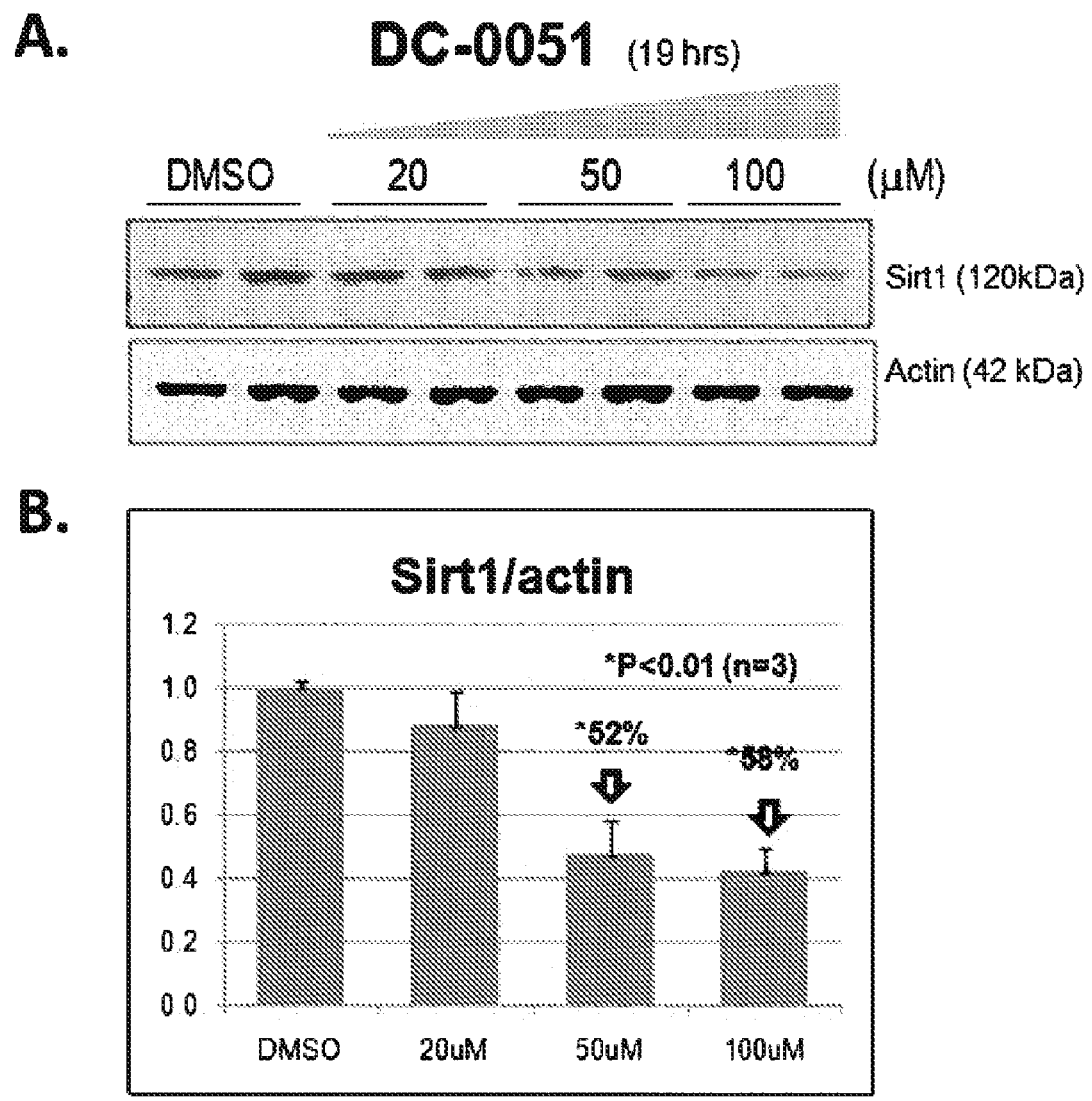
FIG. 2 is a photo and a graph showing effects of compound DC-0051 on expression of Sirt1 in cultured human brain neuroblastoma SK—N—SH cells that stably transfected with the human wild type APP isoform 695 (SKNSH-APP cells) as assessed by Western analysis.

FIGS. 2A-B show that compound DC-0051 reduce levels of Sirt1 in SKNSH-APP cell cultures as assessed by Western analysis. (A) SKNSH-APP cells were treated with 0 (DMSO vehicle control), 20, 50, and 100 μM of DC-0051 in 6-well plates for 19 hrs. Each condition was in triplicate (only duplicate was shown). After incubation, cell lysates were collected and analyzed by Western analysis for Sirt1 (Top panel). The membrane was then stripped and re-probed for beta-actin (Bottom panel), Reduced levels of Sirt1 were found in cells treated with compound DC-0051, when compared to DMSO vehicle control. The reduction was dose-dependent. Levels of beta-actin were shown in the bottom panel. (B) Quantitative densitometry analysis of (A) was performed and the data were normalized to levels of beta-actin. The results showed that a 52-58% significant reduction of Sirt1 levels was observed in lysates of cells treated with 50-100 μm of DC-0051 (P<0.01), when compared to vehicle controls. The results suggest that compound DC-0051 can reduce levels of Sirt1 in the cell line tested.

Figure 3:
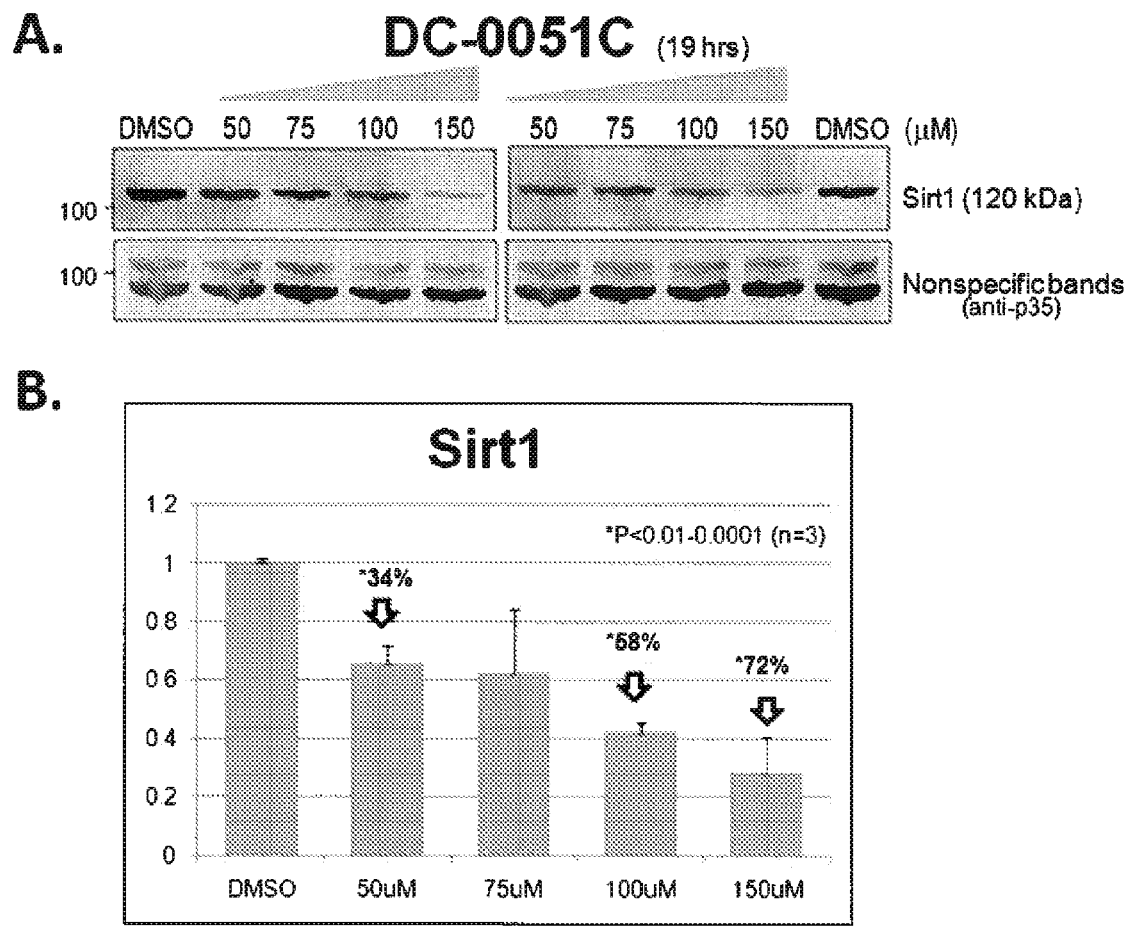
FIG. 3 is a photo and a graph showing effects of peptide compound DC-0051C on expression of Sirt1 in SKNSH-APP cell cultures as assessed by Western analysis.

FIGS. 3A-B show that compound DC-0051C reduce levels of Sirt1 in SKNSH-APP cell cultures as assessed by Western analysis. (A) SKNSH-APP cells were treated with 0 (DMSO vehicle control), 50, 75, 100 and 150 μM of DC-0051C in 6-well plates for 19 hrs. Each condition was in triplicate (only duplicate was shown). After incubation, cell lysates were collected and analyzed by Western analysis for Sirt1 (Top panel). The membrane was then stripped and re-probed with an antibody specific for p35 (an activator of Cdk5; 35 kDa). Non-specific bands of 90-120 kDa recognized by the anti-p35 antibody were shown in the bottom panel. Reduced levels of Sirt1 were found in cells treated with compound DC-0051C, when compared to DMSO vehicle controls. The reduction was dose-dependent. In contrast, levels of the non-specific bands were not changed. (B) Quantitative densitometry analysis of (A) was performed and the data were normalized to levels of the non-specific protein bands. The results showed that a 34-72% significant reduction of Sirt1 levels was observed in lysates of cells treated with 50-150 μM of DC-0051C (P<0.01-0.0001), when compared to the vehicles controls. The results suggest that compound DC-0051C can reduce levels of Sirt1 in the cell line tested.

The invention claimed is:

1. A method for modulating sirtuin 1 comprising contacting human sirtuin 1 with a compound selected from the group consisting of compounds of the formula:

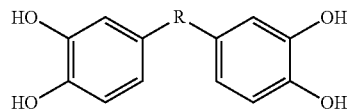

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group.

2. The method of claim 1 where the compound is selected from: 3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl) propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4- dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl) urea; 1-(3,4-dihydroxyphenyl)-3-(3,4-dihydroxyphenethyl) urea; 3-deoxy-3-(3,4-dihydroxybenzyl)aminoepicatechin; 3-deoxy-3-(3,4-dihydroxyphenethyl)aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol; the methylenedioxy analogs and pharmaceutically acceptable esters of compounds and the pharmaceutically acceptable salts of the compounds.

3. The method of claim 1 where the compound is 3,4-dihydroxybenzoic acid 3,4-dihydroxyanilide.

4. A method of neuroprotection for a mammal suffering from a neurodegenerative disease the method comprising administration of a compound to the mammal suffering from a neurodegenerative disease, the compound selected from the group consisting of compounds of the formula:

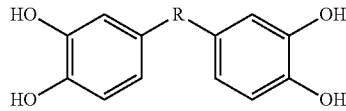

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group.

5. The method of claim 4 where the compound is selected from; 3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethylethylenediamine; 2,5-bis(3,4-dihydroxybenzyl)-2,5-diaza[2.2.1]bicycloheptane; N,N'-bis(3,4-dihydroxybenzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; dihydroxybenzyl)isoquinoline-3-carboxylic acid 3,4-dihydroxyphenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl) methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl) oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-dinza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)pyridine; 2,5-bis(3,4-dihydroxybenzyl)thiophene; 2,3-bis(3,4-dihydroxybenzyl) thiophene; 1,2-bis(3,4-dihydroxyphenyl)cyclohexane; 1,4-bis(3,4-dihydroxyphenyl)cyclohexane; 3,7-bis(3,4-dihydroxyphenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxybenzylamide; 3,4-dihydroxyphenoxyacetic acid 3,4-dihydroxyphenethylamide; 3,4-dihydroxybenzoic acid p-(3,4-dihydroxyphenoxy) anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxybenzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzylamide; 3,4-dihydroxyphenylacetic acid 3,4-dihydroxyphenethylamide; dihydroxyphenyl)propionic acid 3,4-dihydroxyanilide; 3-(3, 4-dihydroxyphenyl) propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic add 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzylamide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxybenzyl)-3,4-dihydroxyphenethylamide; tris(3,4-dihydroxybenzyl)amine; 1,3-bis(3,4-dihydroxyphenyl)urea; 1-(3,4-dihydroxyphenyl)-3-(3,4-dihydroxybenzyl) urea; 1-(3,4-dihydroxyphenyl)-3-(3,4-dihydroxyphenethyl) urea; 3-deoxy-3-(3,4-dihydroxybenzyl)aminoepicatechin; 3-deoxy-3-(3,4-dihydroxyphenethyl)aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol; the methylenedioxy analogs and pharmaceutically acceptable esters of compounds and the pharmaceutically acceptable salts of the compounds.

6. The method of claim 4 where the compound is 3,4-dihydroxybenzoic acid 3,4-dihydroxyanilide.

7. The method of claim 4 where the neurodegenerative disease is selected from the group consisting of Alzheimer's disease, Huntington's disease, Amyotrophic lateral sclerosis, frontotemporal dementia, Parkinson's disease, multiple system atrophy, progressive supranuclear palsy, corticobasal degeneration and dementia with Lewy bodies.

* * * * *